US005660167A

United States Patent [19]

Ryder

[11] Patent Number: 5,660,167

[45] Date of Patent: Aug. 26, 1997

[54] DUAL NOZZLE NEBULIZER

[76] Inventor: Steven L. Ryder, 1334 W. Woodcrest Ave., Fullerton, Calif. 92633

[21] Appl. No.: 460,830

[22] Filed: Jun. 5, 1995

Related U.S. Application Data

[63] Continuation of Ser. No. 109,658, Aug. 20, 1993, abandoned, which is a continuation-in-part of Ser. No. 864,483, Apr. 7, 1992, abandoned, which is a continuation-in-part of Ser. No. 650,451, Feb. 4, 1991, abandoned.

[51] Int. Cl.[6] .................... A61M 11/00

[52] U.S. Cl. .................... 128/200.21; 128/200.14; 128/203.12

[58] Field of Search .................... 128/200.21, 200.14, 128/200.18, 203.12, 203.25, 205.11, 205.24; 239/338

[56] References Cited

U.S. PATENT DOCUMENTS

| | | | |
|---|---|---|---|
| 1,294,246 | 2/1919 | Dorment | 239/338 |
| 2,993,652 | 7/1961 | Curry . | |
| 3,525,476 | 8/1970 | Boling | 239/338 |
| 3,724,454 | 4/1973 | Brown . | |
| 3,809,080 | 5/1974 | Deaton . | |
| 3,836,079 | 9/1974 | Huston | 239/74 |
| 3,864,326 | 2/1975 | Babington . | |
| 4,007,238 | 2/1977 | Glenn . | |
| 4,054,622 | 10/1977 | Lester | 128/200.18 X |
| 4,150,071 | 4/1979 | Pecina . | |
| 4,190,046 | 2/1980 | Virag . | |
| 4,195,044 | 3/1980 | Miller . | |
| 4,206,160 | 6/1980 | Suddendorf | 239/338 X |
| 4,231,973 | 11/1980 | Young | 239/338 X |
| 4,243,396 | 1/1981 | Cronenberg | 128/203.16 X |
| 4,560,519 | 12/1985 | Cerny . | |
| 4,595,002 | 6/1986 | Michaels | 128/200.21 |
| 4,612,926 | 9/1986 | Bolarsky | 128/200.21 |
| 4,629,590 | 12/1986 | Bagwell . | |
| 4,674,491 | 6/1987 | Brugger et al. . | |
| 4,911,157 | 3/1990 | Miller . | |
| 5,241,954 | 9/1993 | Glenn . | |

FOREIGN PATENT DOCUMENTS

| | | | |
|---|---|---|---|
| 513052 | 10/1928 | Germany | 239/338 |
| 879737 | 10/1961 | United Kingdom . | |

*Primary Examiner*—V. Millin
*Assistant Examiner*—William J. Deane, Jr.
*Attorney, Agent, or Firm*—Swanson & Bratschun, LLC

[57] ABSTRACT

A device for entraining a liquid into a carrier gas comprises a hollow cylindrical body having an inlet chamber separated from the interior of the body by a partition. A first nozzle and second nozzle are each supported in the partition and interconnect the inlet chamber and the body interior. A passageway connects a reservoir to the first nozzle so that a first stream of carrier gas flowing through the first nozzle aspirates a liquid within the reservoir and entrains the liquid therein. A second stream of carrier gas flows through the second nozzle and mixes with the first steam in the interior of the body, thereby forming a resultant carrier gas mixture that is lower in liquid concentration than obtainable by having the first nozzle alone. An air inlet opening with an adjustable cover communicates between the interior of the body and its exterior. The air inlet opening is located adjacent the discharge ends of the nozzles to draw air into the resultant carrier gas mixture to dilute the concentration of carrier gas. The enclosure is V-shaped, the reservoir being a separable container that attaches thereto and, when empty, may be detached and replaced with a new reservoir. A drain opening is formed in the enclosure at its lowest point and aligns with a vent opening of the container when the container is fully engaged with the enclosure, thereby maintaining a constant pressure over the liquid in the container and allowing condensed liquid to drain back into the container.

9 Claims, 2 Drawing Sheets

DUAL NOZZLE NEBULIZER

REFERENCE TO RELATED APPLICATIONS

This is a continuation of application(s) Ser. No. 08/109,658 filed on Aug. 20, 1993, now abandoned, which is a continuation-in-part of application Ser. No. 07/864,483, which was filed Apr. 7, 1992, now abandoned, which was a continuation-in-part of application Ser. No. 650,451, filed Feb. 4, 1991, now abandoned.

FIELD OF THE INVENTION

This invention relates to a device foe atomizing a liquid and more particularly to a medical nebulizers for atomizing a liquid within a flow of pressurized carrier gas.

BACKGROUND OF THE INVENTION

Nebulizers used in medical applications typically entrain a medical liquid or water into a high-velocity flow of pressurized carrier gas, such as oxygen, in order to atomize the liquid into a fine mist or aerosol within the carrier gas. The atomized liquid is entrained and carried in the gas stream through a delivery tube to a patient some distance away for inhalation.

Currently available nebulizers include a housing with a carrier gas input nozzle, a reservoir opening and an output opening. A relatively high velocity flow of carrier gas enters the housing through the carrier gas input nozzle. A reservoir port is located within the housing at the output side of the nozzle, the flow of carrier gas being directed across and slightly towards the reservoir port. Notwithstanding the slightly increased "back pressure" within the enclosure that this non-linear carrier gas flow creates, considerable liquid is still drawn into the flow of carrier gas through the reservoir port by virtue of the relatively low pressure created within the housing by the high velocity flow of carrier gas. The liquid is subsequently atomized into a fine mist and the entrained atomized liquid is carried in the carrier gas stream to the patient.

An additional feature found on many currently available nebulizers is an adjustable air inlet opening in the housing adjacent the carrier gas input nozzle. This opening allows air to be drawn into the housing to be mixed with the carrier gas stream in addition to the liquid to reduce the concentration of carrier gas in the resultant mixture. As the most commonly used carrier gas in medical nebulizers is oxygen and since many patients, such as those suffering from emphysema, cannot or need not be exposed to high concentrations of oxygen, this feature often eliminates a need to initially dilute the oxygen carrier gas with pressurized air. As a result, complicated air pressurizing and mixing apparatus need not be used.

While nebulizers have improved significantly over the years, several significant drawbacks still exist with current nebulizer designs. For example, patients with emphysema are quite sensitive to even moderate concentrations of oxygen inhalation. Air has an approximate oxygen concentration of 21%. With the adjustable air inlet opening, current nebulizer designs produce a minimum oxygen concentration of about 28% in the resultant inhalation mixture, and more frequently produce a minimum oxygen concentration of 30%. Oxygen sensitive patients require an even lower minimum oxygen concentration in the inhalation mixture and, consequently, complicated air pressurizing and mixing apparatus are necessary in order to mix air with the pressurized oxygen before the carrier gas enters the nebulizer. This introduces unwanted complexity and cost to the patient undergoing treatment.

Another significant drawback to current nebulizer design is that the nebulizer is designed to attach to a carrier gas valve fixture on the wall in the patient's room thus making movement of the nebulizer set-up difficult and requiring that the patient be disconnected while being transported.

Another disadvantage with current nebulizer design is the relatively long delivery tube between the nebulizer at the fixed wall carrier gas valve and the patient. this results in low spots in the delivery tube where liquid condensation from the resultant carrier gas mixture accumulates. This condensation must be constantly monitored to prevent occlusion of the tubing resulting in possible loss of oxygen and aerosol flow to the patient. Moreover such condensation in the tubing results in the loss of medication and leads to excessive use of medication.

Accordingly there is a need for a portable nebulizer that entrains a greater amount of air into the inhalation mixture thus controllably allowing for decrease of the concentration of carrier gas and liquid medication and that reduces the amount of liquid waste and the need for constant monitoring of the nebulizer set-up.

SUMMARY OF THE INVENTION

The nebulizer of the present invention comprises a hollow body having an interior and an inlet chamber. The inlet chamber communicates with a source of pressurized carrier gas. At least a pair of nozzles communicate between the interior and the inlet chamber for leading the carrier gas through both of the nozzles from the inlet chamber to the interior of the outlet chamber. At least one of the nozzles is connected by passage means to a source of liquid to be entrained in the carrier gas by the flow of carrier gas through the nozzle. An adjustable air inlet is located adjacent the outlets of the nozzles which provides for controllably adjusting the quantity of air which is drawn into the housing responsive to the Venturi effect of the flow of the carrier gas at the nozzle openings into the outlet chamber.

By introducing the carrier gas into the outlet chamber through more than one nozzle, the pressure in the body is reduced more than in the case of nebulizers of conventional design. This results in the entrainment of more air through the air inlet and with the air inlet fully open the concentration of the carrier gas in the stream exiting the device is reduced to about 26% of the mixture of air and carrier gas. By the same token, while reducing the concentration of carrier gas without reducing the total volume of carrier gas used, the total flow of the gas mixture to the patient is increased.

In another embodiment of the invention, the device incorporates a pair of nozzles both of which are connected to the source of liquid as well as communicating with the carrier gas.

In a preferred embodiment of the invention, the body of the device is tubular and is V-shaped to define low point for the collection of condensation. A drain is provided to remove the condensed liquid from the interior of the device and preferably the drain communicates with the source of liquid for returning the condensed liquid for reuse. The V-shape permits the device to be attached directly to the patient's bed frame or rail and eliminates the need for a separate liquid drainage bag.

DESCRIPTION OF THE DRAWINGS

FIG. 1 is a left side elevation view if the invention, illustrating a reservoir container attached to an enclosure of the invention and a partial cut-away view of the enclosure;

DESCRIPTION OF THE INVENTION

Figure 1:
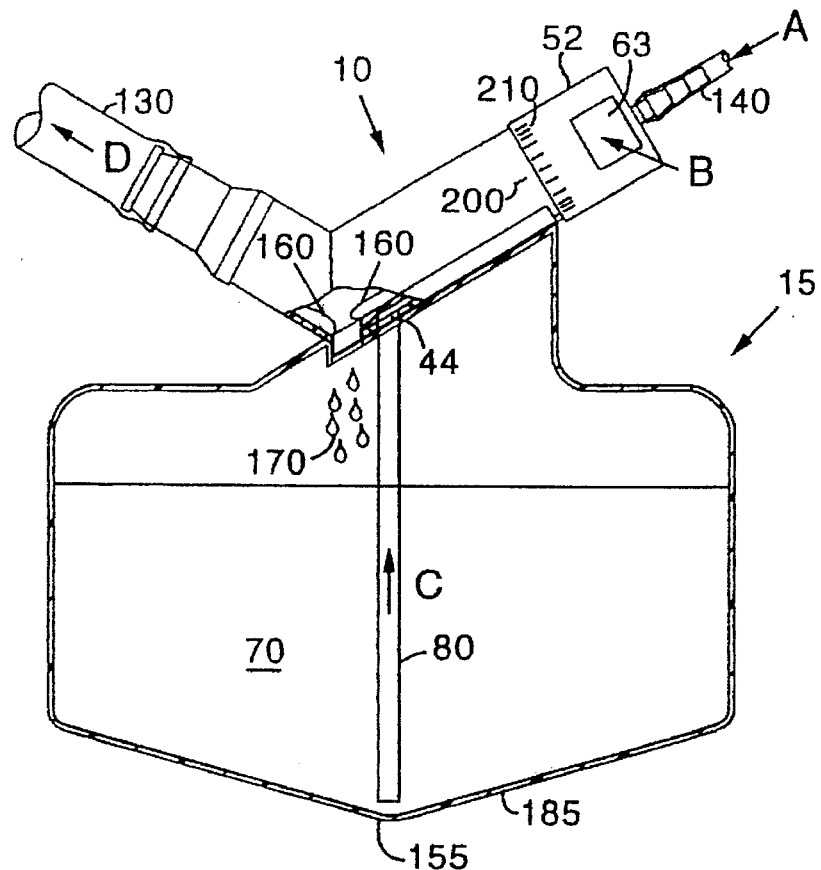
Figure 2:
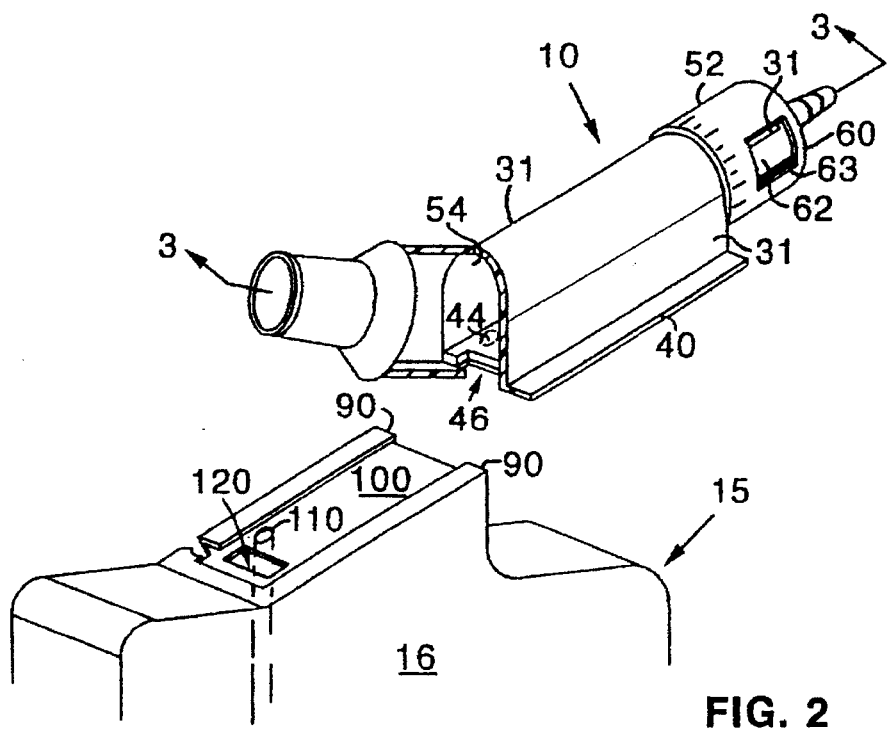
FIG. 2 is a perspective illustration of the invention, illustrating the reservoir container detached from the enclosure of the invention.
Figure 3:
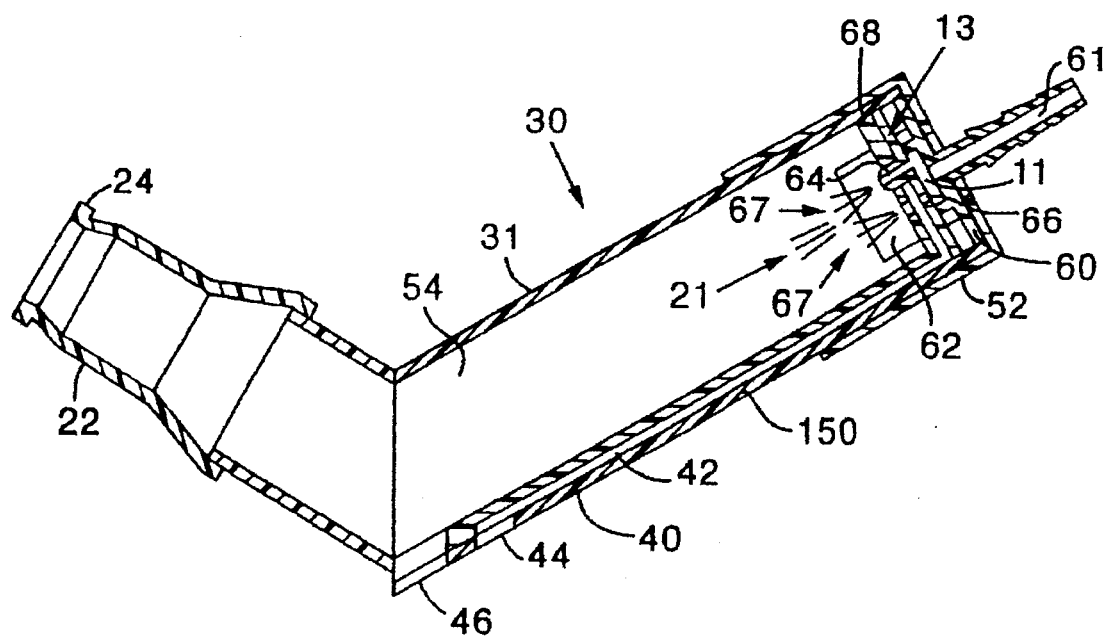
FIG. 3 is a cross sectional view of the invention taken, generally along lines 3—3 of FIG. 2.

FIG. 1–3 illustrate a device 10 for entraining a liquid 70 into a carrier gas 61. A hollow, cylindrical body 30, preferably V-shaped, formed of durable plastic material, has top and side walls 31, an end wall 60 and a bottom wall 150, which cooperate to define an interior 54. The interior 54 is open at the opposite end 24. The open end 24 and the end wall 60 are adapted for connection of a tubulation 140,130 for ingress A (FIG. 1) of the carrier gas 61 and for the egress D (FIG. 1) of a dilute stream of carrier and entrained liquid. A partition 13 (FIG. 3) is spaced from the end wall 60 to define an inlet chamber 11. A first nozzle 66 and a second nozzle 64, each supported by the partition 13, provide fluid communication from the inlet chamber 11 and discharge into the interior 54. Both of the nozzles 66 and 64 serve to transfer a stream 67 of the carrier gas from the inlet chamber 11 to the interior 54 of the body 30. A passageway 42 connects the first nozzle 66 to a reservoir 15 containing the liquid 70 so that the stream 67 of carrier gas flowing through the first nozzle 66 causes the aspiration of the liquid 70 into the first nozzle 66 and entrains the liquid 70 into the stream 67 of the carrier gas flowing therethrough. The stream 67 of the carrier gas flowing through the nozzle 64 is combined in the interior 54 of the body 30 with the stream carrying entrained liquid from the nozzle 66.

It will be understood that the invention is not limited to two nozzles but may employ any number of nozzles as long as at least the first nozzle 66 is interconnected with the reservoir 15 for entrainment of the liquid 70.

An opening 62 in the wall 31 adjacent the end wall 60 provides communication between the interior 54 at the discharge outlet of the nozzles 64, 66 and the exterior of the body 30 for aspiration B (FIG. 1) of air for mixing with each stream 67 of carrier gas. A rotatable closure 52 covers the end portion of the body adjacent the end wall 60 and the opening 62. The closure 52 is provided with a corresponding opening 63 which can be aligned with the opening 62. Preferably, the closure 52 has formed therein registration marks 210 for aligning with a registration mark 200 on the body 30 to aid in aligning the corresponding openings 62 and 63 for control of the quantity of air drawn into the interior 54, and hence provides control over the dilution of the carrier gas and entrained liquid in the resultant gas mixture flowing out of the device 10.

Preferably, the device 10 is separable from the reservoir 15. A top surface 100 of the reservoir 15 has L-shaped members 90 adapted to slidably receive extensions 40 of the bottom wall 150 of the interior 54 for removably connecting the interior 54 and the reservoir 15. The reservoir 15 may be discarded when empty and replaced by a new reservoir 15 containing the liquid 70. The separable reservoir 15 has an enclosed space 16 for storing the liquid 70. an outlet opening 110 for withdrawing the liquid 70 from the bottom of the enclosed space 16 by suction C (FIG. 1) through suction tube 80 connected thereto, a vent 120 for maintaining constant pressure above the liquid 70, and an attachment means 90 for attaching to a securing means 40 of the interior 54. A bottom wall 150 of the reservoir 15 is sloped such that a low point 155 is formed adjacent to the suction tube 80 to enable continuous suction until most of the liquid 70 has been aspirated. During manufacture of the reservoir 15, a thin plastic seal, not shown, may be used to form an air-tight seal on the top surface 100 of the reservoir 15 for sterilization purposes, such thin plastic seal being easily peeled off before use.

Preferably the interior 54 has a drain opening 46 therein which, when the reservoir 15 is attached to the interior 54, aligns with the vent 120 of the reservoir 15 so that condensed liquid 160, 170 will return to the reservoir 15 if the liquid 70 condenses out of the carrier gas plus liquid plus air mixture 21, and so that a constant pressure will be maintained over the liquid 70 in the reservoir 15, facilitating the removal of the liquid 15.

Figure 4:
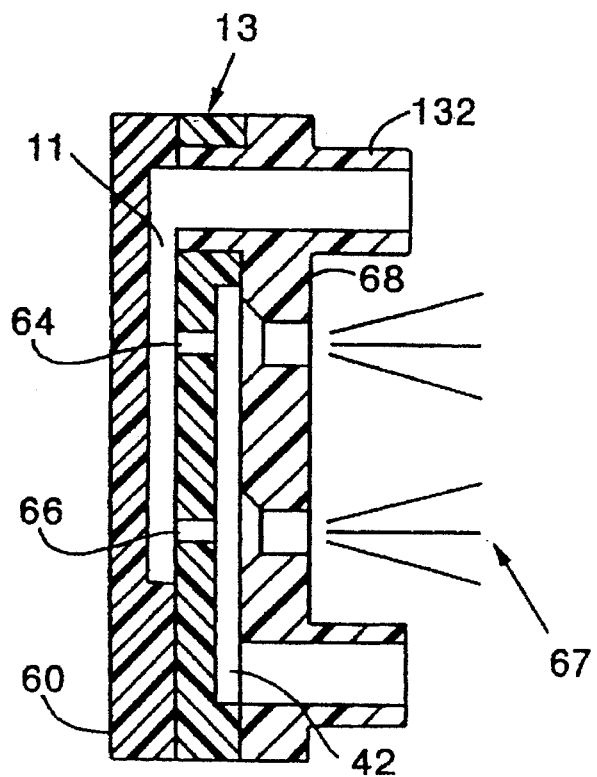
FIG. 4 is a sectional view, partially broken away for compactness of illustration, of an embodiment of the invention where all nozzles are in communication with a source of liquid.

Referring to FIG. 4 where like reference numbers designate like parts, there is illustrated another embodiment of the invention in which liquid is by both of the nozzles 64 and 66. As shown, the partition 13 defines the inlet chamber 11 as described in connection with FIG. 1. The carrier gas enters the inlet chamber 11 through a tube 132 which communicates with a source of carrier gas (not shown). A passageway 42 extends through the partition for communication with the bore of both of the nozzles 64 and 66. The stream 67 of carrier gas through the nozzles causes aspiration of the liquid 70 into both nozzles and entrains the liquid into the stream flowing through both nozzles.

In the preferred mode of the invention, the device 10 is suspended by support means, not shown, to a patient3 s bed. at a lower level then the patient, thereby ensuring that any liquid 160 that is condensed within tube 130 will flow downwardly, through the drain opening 46, and into the reservoir 15 for recycling. In addition, the interior 54 has a liquid inlet opening 44 which, when the reservoir 15 is attached to the interior 54, aligns with the outlet opening 110 of the reservoir 15 so that the liquid 70 may be drawn from the enclosed space 16 into the suction tube 80, through the outlet opening 110 of the reservoir 15 into the liquid inlet opening 44 of the interior 54, into the passageway 42, and subsequently into the first nozzle 66 so as to be entrained into the stream 67 of the carrier gas within the first nozzle 66.

While the invention has been described with reference to a preferred embodiment, it is to be clearly understood by those skilled in the art that the invention is not limited thereto. For example, such nebulizer means may be useful in non-medical applications such as the atomization of other liquids. Thus, the scope of the invention is to be interpreted only in conjunction with the appended claims.

Having described the invention I claim:

1. A device for entraining a liquid into a carrier gas, comprising:

a. a hollow cylindrical body having walls including an end wall which cooperate to define an interior, an open end of said body opposite the end wall, and a partition spaced apart from the end wall cooperating with the end wall to define an inlet chamber;

b. means for connecting the inlet chamber to a source of carrier gas;

c. at least a pair of nozzle bores extending through the partition, one end of each nozzle bore opening to the inlet chamber and an opposite discharge end opening to the interior of said body to carry a stream of said carrier gas through each said nozzle bore for discharge into the interior;

d. means for communicating a source of liquid to be aspirated with at least one of the nozzle bores for aspiration of the liquid;

e. an opening in a wall of the body adjacent the discharge end of the nozzle bores providing communication from the exterior to the interior of said body, a rotatable closure covering an end portion of the body adjacent the end wall and the opening, the closure being provided with a corresponding opening for alignment with the opening and for intermediate positions with the corresponding opening out of alignment with the opening in said body, the opening being situated so that a carrier gas stream exiting the nozzle bores draws exterior air through the opening in the body when the opening is at least partially aligned with the corresponding opening of the closure to dilute the carrier gas, the carrier gas streams being substantially unobstructed as they enter the interior so as to minimize reduction of their velocity in proximity to the opening.

2. The device of claim 1 wherein said means for connection to a source of a liquid to be aspirated comprises a reservoir consisting of a separable container, a top surface of the container being adapted for mounting of said body thereon and a passageway in said body communicating between the reservoir and the bore of at least one of the nozzles.

3. A device containing a liquid for aspiration comprising a hollow body and a reservoir, said reservoir having an enclosed space including a bottom for storing said liquid, an outlet opening for withdrawing said liquid from the bottom of the enclosed space by a suction tube, a vent for maintaining constant pressure above the liquid, and a means for attachment of the reservoir to the hollow body, the hollow body formed as a cylindrical shell having an interior end defining opposing open ends, each said open end formed as a fitting for attachment of a tubulation thereto, the shell supporting a partition adjacent one end to define an inlet chamber adjacent said one end, the partition having a first and a second nozzle, each nozzle having a bore with a first discharge end which opens to the interior of the body and a second opposite end which opens to the inlet chamber for communication between the inlet chamber and the interior of the body, a line extending from the reservoir and opening to the bore of the first nozzle, the shell having a drain communicating with the reservoir and an air inlet opening between the interior of the shell and an exterior of the shell adjacent the discharge end of the nozzles, an adjustable closure for the air inlet movable to positions covering portions of the air inlet, the exterior of the shell having means for cooperation with the attachment means of the reservoir for securing the reservoir to the body so that the drain opening is aligned with the vent of the reservoir, whereby the injection of the carrier gas into the inlet chamber through one of said open ends forces a first stream of carrier gas through the first nozzle causing the entrainment of the liquid delivered to the bore of the first nozzle by reduced pressure in the line and a second stream having no entrainment of the liquid or other obstruction as it exits the second nozzle, the first and second streams and outside air mixing in the interior of the body.

4. The device of claim 1 wherein the bores of at least a pair of the nozzles are in communication with a source of a liquid for entrainment and aspiration in the stream of carrier gas in said nozzles.

5. A device for entraining a liquid into a carrier gas comprising:

a body having a side wall, a closed end and an open end defining an interior wall, the body further including a body opening in the side wall between the opened end and closed ends for admitting air into the body interior;

a first partition in the housing interior proximate the closed end defining an inlet chamber between the closed end and the first partition;

a second partition in the housing interior proximate the first partition defining a liquid delivery passageway between first and second partitions and a mixing chamber between the second partition, the side wall and the open end of the housing;

the first partition including at least two primary nozzles providing fluid communication between the inlet chamber and the mixing chamber, at least one of the primary nozzles extending between the inlet chamber and the liquid delivery passageway, and the second partition including a secondary nozzle axially aligned with each primary nozzle which extends between the inlet chamber and the liquid delivery channel;

means for connecting the inlet chamber to a source of carrier gas; and means for connecting the liquid delivery channel to a source of liquid to be aspirated.

6. The device of claim 5 further comprising a rotatable closure covering the body and the body opening, the rotatable closure having a closure opening which is rotatable into and out of alignment with the body opening to control the amount of exterior air drawn through the body opening and thereby the extent to which the carrier gas streams are diluted by the exterior air.

7. The device of claim 6 wherein at least one of the carrier gas streams is unobstructed until it passes the body opening.

8. The device of claim 7 wherein the carrier gas streams are at a velocity sufficient to draw in a volume of exterior air to provide for carrier gas concentrations of between about 26% and 100% as the closure opening is brought into and out of alignment with the body opening.

9. A device for entraining a liquid into a carrier gas, comprising:

a. a hollow cylindrical body having walls including an end wall which cooperate to define an interior, an open end of said body opposite the end wall, and a partition spaced apart from the end wall cooperating with the end wall to define an inlet chamber:

b. means for connection of the inlet chamber to a source of carrier gas;

c. means for connection to a source of a liquid to be aspirated;

d. at least a pair of nozzles, each nozzle having a bore extending through the partition, one end of each nozzle bore opening to the inlet chamber and a second opposite discharge end opening to the interior of said body to carry a stream of said carrier gas through each said nozzle for discharge into the interior without obstruction to said stream of said carrier gas in said interior, the bore of at least one of the nozzles being in liquid communication with said means for connection to a source of liquid to be aspirated for entraining the liquid to be aspirated in a carrier gas stream;

e. an opening in a wall of the body adjacent the discharge end of the nozzles providing communication from the exterior to the interior of said body, the opening being positioned to provide a draw of exterior air through the opening for mixing the carrier gas stream and entrained liquid with the exterior air in the body interior to dilute the carrier gas; and f. a closure covering an end portion of the body adjacent the end wall and the opening, the closure being provided with a corresponding opening for alignment with the opening and for intermediate positions with the corresponding opening out of alignment with the opening in said body, the closure controlling the amount of exterior air entering the interior to vary the concentration of carrier gas.

* * * * *